US012221650B2

United States Patent
Cho

(10) Patent No.: US 12,221,650 B2
(45) Date of Patent: Feb. 11, 2025

(54) METHOD OF DETECTING RNA

(71) Applicant: XENOHELIX CO., LTD, Jeonju-si (KR)

(72) Inventor: Seok Keun Cho, Incheon (KR)

(73) Assignee: XENOHELIX CO., LTD, Jeonju-si (KR)

( * ) Notice: Subject to any disclaimer, the term of this patent is extended or adjusted under 35 U.S.C. 154(b) by 0 days.

(21) Appl. No.: 17/136,793

(22) Filed: Dec. 29, 2020

(65) Prior Publication Data

US 2021/0381034 A1 Dec. 9, 2021

(30) Foreign Application Priority Data

Jun. 3, 2020 (KR) .................. 10-2020-0066932

(51) Int. Cl.
*C12Q 1/68* (2018.01)
*C12Q 1/6825* (2018.01)
*C12Q 1/6855* (2018.01)

(52) U.S. Cl.
CPC ......... *C12Q 1/6825* (2013.01); *C12Q 1/6855* (2013.01); *C12Q 2563/179* (2013.01); *C12Q 2563/185* (2013.01)

(58) Field of Classification Search
CPC ............ C12Q 1/6825; C12Q 1/6855; C12Q 2563/179; C12Q 2563/185; C12Q 1/6869; C12Q 1/6874; C12Q 2525/191
See application file for complete search history.

(56) References Cited

U.S. PATENT DOCUMENTS

| 7,666,593 | B2 | 2/2010 | Lapidus |
| 9,260,753 | B2 * | 2/2016 | Xie ................. C12Q 1/6874 |
| 2007/0077582 | A1 | 4/2007 | Slepnev |
| 2010/0316991 | A1 * | 12/2010 | Roth ................. C12N 7/00 |
| | | | 435/235.1 |
| 2016/0355870 | A1 | 12/2016 | Fang et al. |
| 2017/0107582 | A1 | 4/2017 | Eloit et al. |
| 2020/0063190 | A1 | 2/2020 | Chenchik et al. |
| 2021/0002716 | A1 | 1/2021 | Weng et al. |
| 2021/0291135 | A1 | 9/2021 | Barnard et al. |
| 2021/0355531 | A1 | 11/2021 | Weng et al. |

FOREIGN PATENT DOCUMENTS

| EP | 1544309 A1 | 6/2005 |
| JP | 2016-513958 A | 5/2016 |
| JP | 2018-537955 A | 12/2018 |
| JP | 2019-531710 A | 11/2019 |

(Continued)

OTHER PUBLICATIONS

Cornelis Senne et al, Forensic SNP Genotyping using Nanopore MinION Sequencing, Feb. 3, 2017, Scientific Reports, vol. 7, No. 41759, pp. 1-5. (Year: 2017).*

(Continued)

*Primary Examiner* — Jehanne S Sitton
(74) *Attorney, Agent, or Firm* — Sughrue Mion, PLLC

(57) ABSTRACT

The present invention relates to a method of analyzing and detecting RNA. In particular, the present invention is capable of analyzing RNA with short base sequences while quantitatively detecting RNA with high sensitivity and accuracy, and thus can be widely used for diagnosis of various diseases such as infectious diseases and cancer.

6 Claims, 7 Drawing Sheets

Specification includes a Sequence Listing.

(56) References Cited

FOREIGN PATENT DOCUMENTS

| KR | 10-2010-0075524 A | 7/2010 |
|---|---|---|
| WO | 95/32306 A1 | 11/1995 |
| WO | 2008/094890 A2 | 8/2008 |
| WO | 2018/218222 A1 | 11/2018 |
| WO | 2019/199579 A1 | 10/2019 |

OTHER PUBLICATIONS

Jain et al., The Oxford Nanopore MinION: delivery of nanopore sequencing to the genomics community, Genome Biology, vol. 17: 239, DOI 10.1186/s13059-016-1103-0 (Year: 2016).*
Lopez et al; Nature Communications, vol. 10, 2019, 1-9.*
Notification of Reason for Refusal dated Oct. 20, 2021 from the Korean Patent Office in Korean Application No. 10-2020-0066932.
Kenneth Morabito et al., "Engineering Insights for Multiplexed Real-Time Nucleic Acid Sequence—Based Amplification (NASBA): Implications for Design of Point-of-Care Diagnostics", Mol Diagn Ther, 2013, vol. 17, pp. 185-192 (8 pages total).
Michael D. Gallagher, et al., "Nanopore sequencing for rapid diagnostics of salmonid RNA viruses", Scientific Reports, 2018, vol. 8, No. 16307, pp. 1-9 (9 pages total).
Extended European Search Report issued Jun. 21, 2021 in European Application No. 20217707.7.
Office Action dated Nov. 15, 2022 issued by the Japanese Patent Office in Japanese Application No. 2021-091104.
Jin et al., "Gene Expression Profiling via Multigene Concatemers" PLoS ONE, 2011, vol. 6, Issue 1, e15711, pp. 1-6 (6 pages total).

* cited by examiner

SEQUENCE LISTING

<160> NUMBER OF SEQ ID NOS: 25

<210> SEQ ID NO 1
<211> LENGTH: 22
<212> TYPE: DNA
<213> ORGANISM: Artificial Sequence
<220> FEATURE:
<223> OTHER INFORMATION: Hs-RNaseP sensor DNA

<400> SEQUENCE: 1
aagggagtgc tgacagagac tg                                              22

<210> SEQ ID NO 2
<211> LENGTH: 24
<212> TYPE: DNA
<213> ORGANISM: Artificial Sequence
<220> FEATURE:
<223> OTHER INFORMATION: Hs-U6 sensor DNA

<400> SEQUENCE: 2
atatggaacg cttcacgaat ttgc                                            24

<210> SEQ ID NO 3

```
<211> LENGTH: 20
<212> TYPE: DNA
<213> ORGANISM: Artificial Sequence
<220> FEATURE:
<223> OTHER INFORMATION: COVID-19 ORF7 sensor DNA

<400> SEQUENCE: 3
tacgccgtca ggacaagcaa                                            20

<210> SEQ ID NO 4
<211> LENGTH: 20
<212> TYPE: DNA
<213> ORGANISM: Artificial Sequence
<220> FEATURE:
<223> OTHER INFORMATION: COVID-19 N gene sensor DNA

<400> SEQUENCE: 4
tgcgcgacat tccgaagaac                                            20

<210> SEQ ID NO 5
<211> LENGTH: 20
<212> TYPE: DNA
<213> ORGANISM: Artificial Sequence
<220> FEATURE:
<223> OTHER INFORMATION: COVID-19 RdRp gene sensor DNA

<400> SEQUENCE: 5
atttgttcgc gtggtttgcc                                            20

<210> SEQ ID NO 6
<211> LENGTH: 10
<212> TYPE: DNA
<213> ORGANISM: Artificial Sequence
<220> FEATURE:
<223> OTHER INFORMATION: complementary sequence of Hs-RNaseP barcode
      region

<400> SEQUENCE: 6
ttgtcttcca                                                       10

<210> SEQ ID NO 7
<211> LENGTH: 10
<212> TYPE: DNA
<213> ORGANISM: Artificial Sequence
<220> FEATURE:
<223> OTHER INFORMATION: complementary sequence of Hs-RNaseP barcode
      region

<400> SEQUENCE: 7
tggaagacaa                                                       10

<210> SEQ ID NO 8
<211> LENGTH: 10
<212> TYPE: DNA
<213> ORGANISM: Artificial Sequence
<220> FEATURE:
<223> OTHER INFORMATION: complementary sequence of Hs-U6 barcode region

<400> SEQUENCE: 8
tactaaaatt                                                       10

<210> SEQ ID NO 9
<211> LENGTH: 10
<212> TYPE: DNA
<213> ORGANISM: Artificial Sequence
<220> FEATURE:
<223> OTHER INFORMATION: complementary sequence of Hs-U6 barcode region
```

```
<400> SEQUENCE: 9
aattttagta                                                          10

<210> SEQ ID NO 10
<211> LENGTH: 10
<212> TYPE: DNA
<213> ORGANISM: Artificial Sequence
<220> FEATURE:
<223> OTHER INFORMATION: complementary sequence of COVID-19 ORF7 barcode
      region

<400> SEQUENCE: 10
attcaccatt                                                          10

<210> SEQ ID NO 11
<211> LENGTH: 10
<212> TYPE: DNA
<213> ORGANISM: Artificial Sequence
<220> FEATURE:
<223> OTHER INFORMATION: complementary sequence of COVID-19 ORF7 barcode
      region

<400> SEQUENCE: 11
aatggtgaat                                                          10

<210> SEQ ID NO 12
<211> LENGTH: 10
<212> TYPE: DNA
<213> ORGANISM: Artificial Sequence
<220> FEATURE:
<223> OTHER INFORMATION: complementary sequence of COVID-19 N gene
      barcode region

<400> SEQUENCE: 12
ccagaacaaa                                                          10

<210> SEQ ID NO 13
<211> LENGTH: 10
<212> TYPE: DNA
<213> ORGANISM: Artificial Sequence
<220> FEATURE:
<223> OTHER INFORMATION: complementary sequence of COVID-19 N gene
      barcode region

<400> SEQUENCE: 13
tttgttctgg                                                          10

<210> SEQ ID NO 14
<211> LENGTH: 10
<212> TYPE: DNA
<213> ORGANISM: Artificial Sequence
<220> FEATURE:
<223> OTHER INFORMATION: complementary sequence of COVID-19 RdRp gene
      barcode region

<400> SEQUENCE: 14
tggtggacag                                                          10

<210> SEQ ID NO 15
<211> LENGTH: 10
<212> TYPE: DNA
<213> ORGANISM: Artificial Sequence
<220> FEATURE:
<223> OTHER INFORMATION: complementary sequence of COVID-19 RdRp gene
      barcode region
```

```
<400> SEQUENCE: 15
ctgtccacca                                                              10

<210> SEQ ID NO 16
<211> LENGTH: 23
<212> TYPE: DNA
<213> ORGANISM: Artificial Sequence
<220> FEATURE:
<223> OTHER INFORMATION: Hs_RNaseP Forward primer

<400> SEQUENCE: 16
cggccatcag aaggagatga aga                                               23

<210> SEQ ID NO 17
<211> LENGTH: 22
<212> TYPE: DNA
<213> ORGANISM: Artificial Sequence
<220> FEATURE:
<223> OTHER INFORMATION: Hs_RNaseP Reverse primer

<400> SEQUENCE: 17
aagggagtgc tgacagagac tg                                                22

<210> SEQ ID NO 18
<211> LENGTH: 21
<212> TYPE: DNA
<213> ORGANISM: Artificial Sequence
<220> FEATURE:
<223> OTHER INFORMATION: Hs_U6 Forward primer

<400> SEQUENCE: 18
tgctcgcttc ggcagcacat a                                                 21

<210> SEQ ID NO 19
<211> LENGTH: 24
<212> TYPE: DNA
<213> ORGANISM: Artificial Sequence
<220> FEATURE:
<223> OTHER INFORMATION: Hs_U6 Reverse primer

<400> SEQUENCE: 19
atatggaacg cttcacgaat ttgc                                              24

<210> SEQ ID NO 20
<211> LENGTH: 22
<212> TYPE: DNA
<213> ORGANISM: Artificial Sequence
<220> FEATURE:
<223> OTHER INFORMATION: COVID-19 ORF7 Forward primer

<400> SEQUENCE: 20
tcttctggaa catacgaggg ca                                                22

<210> SEQ ID NO 21
<211> LENGTH: 20
<212> TYPE: DNA
<213> ORGANISM: Artificial Sequence
<220> FEATURE:
<223> OTHER INFORMATION: COVID-19 ORF7 Reverse primer

<400> SEQUENCE: 21
tacgccgtca ggacaagcaa                                                   20

<210> SEQ ID NO 22
<211> LENGTH: 20
```

```
<212> TYPE: DNA
<213> ORGANISM: Artificial Sequence
<220> FEATURE:
<223> OTHER INFORMATION: COVID-19 N gene Forward primer

<400> SEQUENCE: 22
aagctttcgg cagacgtggt                                          20

<210> SEQ ID NO 23
<211> LENGTH: 20
<212> TYPE: DNA
<213> ORGANISM: Artificial Sequence
<220> FEATURE:
<223> OTHER INFORMATION: COVID-19 N gene Reverse primer

<400> SEQUENCE: 23
tgcgcgacat tccgaagaac                                          20

<210> SEQ ID NO 24
<211> LENGTH: 20
<212> TYPE: DNA
<213> ORGANISM: Artificial Sequence
<220> FEATURE:
<223> OTHER INFORMATION: COVID-19 RdRp gene Forward primer

<400> SEQUENCE: 24
agctcatggg acacttcgca                                          20

<210> SEQ ID NO 25
<211> LENGTH: 20
<212> TYPE: DNA
<213> ORGANISM: Artificial Sequence
<220> FEATURE:
<223> OTHER INFORMATION: COVID-19 RdRp gene Reverse primer

<400> SEQUENCE: 25
atttgttcgc gtggtttgcc                                          20
```

METHOD OF DETECTING RNA

CROSS-REFERENCE TO RELATED APPLICATION

This application claims priority to and the benefit of Korean Patent Application No. 2020-0066932, filed on Jun. 3, 2020, the disclosure of which is incorporated herein in its entirety by reference.

TECHNICAL FIELD

The present invention relates to a method of analyzing and detecting RNA. In particular, the present invention is capable of analyzing RNA with short base sequences while quantitatively detecting RNA with high sensitivity and accuracy, and thus can be widely used for diagnosis of various diseases such as infectious diseases and cancer.

BACKGROUND ART

As the quality of life improves, interest in early diagnosis of diseases is growing. Molecular diagnostic technology directly detects the genetic information (DNA/RNA) of the pathogen causing a disease, and accordingly is gaining attention as a technology that can solve the disadvantages of immunodiagnostic technology which detects indirect factors of the disease.

Also, with the recent coronavirus disease-19 (COVID-19) outbreak, many deaths have occurred worldwide, and the WHO even declares a pandemic of COVID-19. In the case of a disease caused by an RNA virus, further damage is caused by the high mutation incidence rate, and early diagnosis of the infection is further required.

Korean Published Patent No. 10-2010-0075524 discloses a technology for synthesizing a double-stranded DNA from RNA using a DNA primer and detecting the double-stranded DNA. However, the invention only detects the presence of a double-stranded DNA by fluorescence intensity, but does not disclose a technology for detecting in specific values at very low concentrations.

RNA expression patterns are sensitive to early stages of infectious diseases or cancer, and thus show strong advantages in early prediction and detection. Also, since it is possible to test a variety of cancers by simply collecting blood, the burden on the patient's body may be reduced. Further, in addition to the above infectious diseases and cancer, there is an increasing demand for the development of a technology enabling early diagnosis by rapidly detecting RNA with high sensitivity when diagnosing various intractable diseases such as Alzheimer's and Parkinson's disease.

DESCRIPTION OF EMBODIMENTS

Technical Problem

The technical problem to be solved by the present invention is to provide a method of detecting RNA.

Also, the technical problem to be solved by the present invention is to provide a sensor DNA for detecting RNA.

Technical Solution

According to an aspect of the present invention relates to a method of detecting RNA, comprising: a) hybridizing sensor DNA including a complementary sequence of target RNA to be detected with the target RNA; b) polymerizing with a polymerase using the target RNA as a template and the sensor DNA as a primer; c) generating an amplicon by amplifying using a primer corresponding to the strand polymerized in step b); and d) analyzing a sequence of the amplicon.

In one embodiment, the primer in step c) may have a phosphate bound to the 5' end. The primer in step c) is used to produce an amplicon through an amplification reaction, and a base sequence of the primer can be applied without limitation as long as the base sequence can be bound to a strand to be amplified through the phosphate bound to the 5' end.

That is, the base sequence may be changed depending on the target small RNA to be detected or the module region of the sensor DNA.

In one embodiment, when a plurality of amplicons are produced in step c), the method may further comprise d') ligating the produced amplicons.

Through the ligation, the base sequence of the small RNA may be analyzed even with the Oxford Nanopore sequencing system (Oxford Nano) in the related art, which cannot analyze short base sequences.

In one embodiment, after the ligation of the amplicons, the method may further include: attaching adenine (A) to the 3' end by adding a dATP and a DNA polymerase thereto, and as the DNA polymerase, a Taq polymerase may be used, but the present invention is not limited thereto.

In one embodiment, step d') may further comprise: after ligation of amplicons, binding an adaptor for sequencing to both ends of the ligated amplicons. The adaptor is capable of being recognized by a sequencing device, and may be bound by changing the adaptor depending on a sequencing device to be applied, such as an Oxford Nanopore sequencing device and a next generation sequencing (NGS) device.

In one embodiment, the method may further comprise e) analyzing a sequence of the ligated amplicons after step d'). In step e), the sequencing may be Nanopore sequencing.

The nanopore sequencing may mean typical 'nanopore sequencing'. The 'nanopore sequencing' refers to a technique for discriminating various bases by measuring the difference in electrical conductivity while passing a strand of DNA through a biological pore. Since the nanopore sequencing analyzes a base sequence while passing the sequence through pores, the nanopore sequencing has a disadvantage in that a short base sequence cannot be analyzed, and thus cannot be applied to the detection and analysis of short base sequence RNA.

The present invention provides a length that may be analyzed even through the nanopore sequencing by ligating amplicons so that RNA may be detected and analyzed regardless of the length. The present invention may be applied without limitation in sequence analysis techniques.

In one embodiment, the method may further comprise, before step a), designating a unique barcode region in the target RNA. The barcode region may be appropriately designated according to the type of target RNA, and a complementary sequence of the barcode region may be included in the polymerized DNA strand through a DNA polymerization process in which the target RNA is used as a template. Thereafter, the presence or absence of a complementary sequence region of the barcode and the number of complementary sequence regions of the barcode to be detected may be checked to correspond to the presence and number of the target RNA.

In one embodiment, the amplicon may be amplified to include a sequence complementary to the barcode region of the target RNA. When each target RNA has a unique barcode region, each amplicon generated during the process of generating the amplicon through amplification may include a sequence region complementary to the barcode of the target RNA in each amplicon.

In one embodiment, the 'detection' may be capable of quantitatively detecting up to the number of target RNAs by measuring the number of amplicons.

In one embodiment, the number of amplicons may be confirmed by measuring the number of sequences complementary to the barcode region of the target RNA included in the amplicon.

In an exemplary embodiment of the present invention, the RNA detected using human blood not infected with COVID-19 and human blood infected with COVID-19 as samples, respectively, is analyzed. In case of mixing 1 fmol of each of the several types of sensors with the total RNA extracted from the human blood not infected with COVID-19, it is confirmed that many RNAs generally present in the human body are detected whereas ORF7 of COVID-19 is not detected (FIG. 4). Also, in case of mixing 500 amol of each of the several types of sensors with the total RNA extracted from the human blood infected with COVID-19, it is confirmed that COVID-19 ORF7, COVID-19 N gene and COVID-19 RdRp show quantitative levels (FIG. 5). In particular, it is confirmed that the amount quantitatively detected varies according to the coronavirus gene region, and thus may be applied to diagnosing the infection level by identifying the expression level of the gene region. No technologies for determining the infection level by measuring the expression level of the gene site of the RNA virus have been previously reported.

Further, the features of the method of detecting RNA and the sensor DNA used for detection in the present invention show a very low detection limitation at levels of femtomole (fmol) and attomole (amol), and thus the sensitivity and accuracy are remarkably superior to the conventional technologies for detecting RNA.

Another aspect of the present invention relates to a sensor DNA for detecting RNA, comprising: a RNA sensing region comprising a complementary sequence of a target RNA.

In one embodiment, the sensor may be used as a primer in the DNA polymerization process for RNA detection.

In one embodiment, the sensor may be a nanopore sensor. The 'nanopore sensor' is a sensor based on nanopores, which means that nanopore sequencing may be applied.

Advantageous Effects of Invention

The method of detecting RNA and the sensor RNA used for detection in the present invention show a very low detection limitation at levels of femtomole (fmol) and attomole (amol), and thus the sensitivity and accuracy are remarkably superior to the conventional technologies for detecting RNA.

Accordingly, the present invention overcomes the detection limitations of the existing technologies such as diagnosis of a disease in individuals such as human, progress of a disease, diagnosis of viral infection in latent period, etc. by enabling molecular diagnosis at a fine level, and thus may be usefully used even for diagnosis at a very early stage or latent period of a disease.

The effect of the present invention is not limited to the aforementioned effects, and it should be understood to include all possible effects deduced from the configuration of the invention described in the detailed description or the claims of the present invention.

DETAILED DESCRIPTION OF EXEMPLARY EMBODIMENTS

Figure 1:
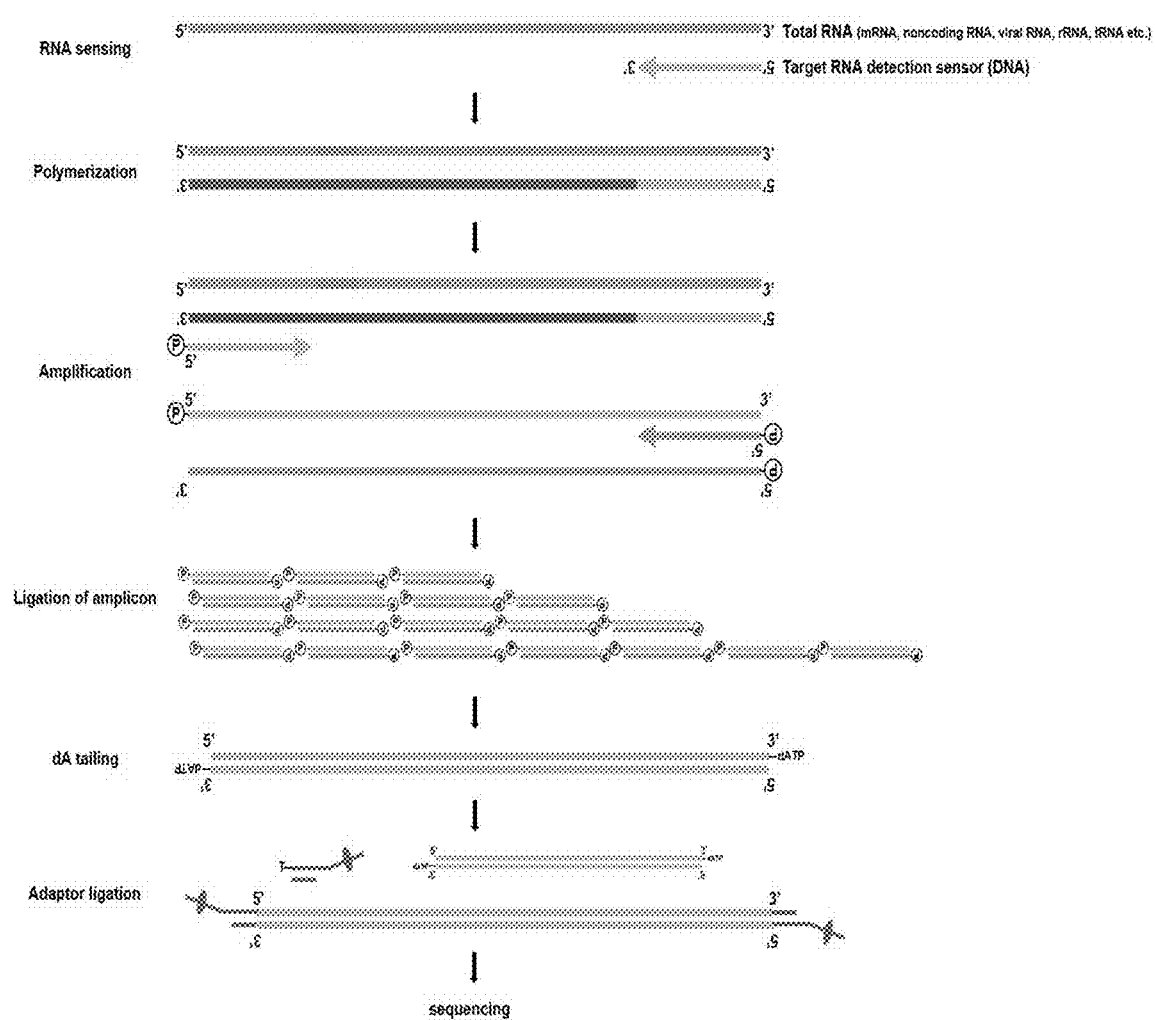
FIG. 1 is shows a schematic view of a method of detecting RNA according to an embodiment of the present invention.

Hereinafter, the present invention will be described in detail through the Examples. However, the following Examples are only for exemplifying the present invention, and the present invention is not limited by the following Examples.

Example 1. Polymerization, Amplification and Sequencing Using Sensor DNA

After mixing the target RNA and the sensor DNA, the sensor DNA sensed the target RNA, and bound to the target RNA, so that the target RNA and the sensor DNA were hybridized.

The sensor DNA comprises a sensing region comprising a complementary sequence of the target RNA. The sensing region senses the target RNA and is hybridized with the target RNA, and thus is referred to as 'sensor DNA' in the present invention.

After hybridizing the target RNA with the sensor DNA, it was polymerized with a DNA polymerase (XenoT-PoL) at 95° C. for 30 seconds and 63° C. for 10 minutes using the target RNA as a template and the sensor DNA as a primer. Then, the sensor and the RNA were disassembled using endonuclease.

A specific sequence of the target RNA may be designated and named with a barcode, and accordingly, a strand polymerized using a sensor DNA as a primer may comprise a region complementary to the barcode. Afterwards, in the detection, the number of target RNAs may be quantitatively measured by counting the number of regions complementary to the target RNA barcode in the polymerized strand.

Thereafter, in order to amplify the polymerized strand, amplicon(s) was/were generated through PCR using a primer to which phosphate bound to the 5' end. The PCR may be performed in the same manner as in typical PCR, and the temperature conditions, cycle number, and the like of the PCR may be appropriately modified and applied depending on the polymerized strand and a sequence of a primer bound to the polymerized strand.

Thereafter, after the produced amplicons were ligated using a DNA ligase, the ligated amplicons were subjected to sequencing.

As an example of sequence analysis, the sensor DNA is a nanopore-based sensor, and sequencing (nanopore sequencing) using a nanopore may be applied to the sequencing. Specifically, after a nanopore adaptor is bound to the ligated amplicons, nanopore sequencing may be performed, and the nanopore sequencing may be performed according to a manual of a known product using the known product. For example, after a sample is loaded onto a Minion chip which is a nanopore sequencing device, the sequencing may be performed.

The accuracy and sensitivity of the detection method of the present invention was confirmed by the following experimental examples, and experiments were exemplarily performed using Hs_RNaseP, Hs-U6, COVID-19 ORF7, COVID-19 N gene, and COVID-19 RdRp as target RNAs to be detected. The sequence of the sensor DNA comprising a complementary sequence of the target RNA for detecting the above exemplary target RNAs is as summarized in Table 1 below. The sequence of the sensor DNA may be modified as needed, and is not limited to the present example.

TABLE 1

| SEQ ID NO. | Target RNA | Sequence of sensor DNA (5'-3') |
| --- | --- | --- |
| 1 | Hs-RNaseP | (Hs-RNaseP sensor) AAGGGAGTGCTGACAGAGACTG |
| 2 | Hs-U6 | (Hs-U6 sensor) ATATGGAACGCTTCACGAATTTGC |
| 3 | COVID-19 ORF7 | (COVID-19 ORF7 sensor) TACGCCGTCAGGACAAGCAA |
| 4 | COVID-19 N gene | (COVID-19 N gene sensor) TGCGCGACATTCCGAAGAAC |
| 5 | COVID-19 RdRp | (COVID-19 RdRp sensor) ATTTGTTCGCGTGGTTTGCC |

For quantitative detection of the exemplary target RNA, the target RNA is designated with a barcode region, and the complementary sequence of the barcode region included in the polymerized DNA strand using the target RNA as a template is summarized in Table 2 below. The target RNA may be quantitatively detected by counting the number of complementary sequences of the barcode region included in the polymerized DNA strand. In particular, the complementary sequence of the barcode region is a part that is counted in quantitative detection, and in consideration of the possibility that there may be strands ligated in the reverse direction when ligating amplicons, the complementary sequence for the two cases of forward direction and reverse direction was counted. By considering the directionality as described above, it was made sure to detect complementary sequences without omitting those ligated in the reverse direction, and further maintain the accuracy of quantitative detection.

The sequence of the barcode region may be modified as needed, and the complementary sequence of the target RNA barcode detected accordingly may also be modified according to the barcode region sequence, and is not limited to the present example.

TABLE 2

| SEQ ID NO. | Target RNA | Complementary sequence of target RNA barcode (5'-3') |
| --- | --- | --- |
| 6 | Hs-RNaseP | TTGTCTTCCA |
| 7 |  | TGGAAGACAA |
| 8 | Hs-U6 | TACTAAAATT |
| 9 |  | AATTTTAGTA |
| 10 | COVID-19 ORF7 | ATTCACCATT |
| 11 |  | AATGGTGAAT |
| 12 | COVID-19 N gene | CCAGAACAAA |
| 13 |  | TTTGTTCTGG |
| 14 | COVID-19 RdRp | TGGTGGACAG |
| 15 |  | CTGTCCACCA |

In addition, exemplarily, the primer sequence in which phosphate is attached at the 5'-end used for amplifying the polymerized strand using the target RNA as a template and the sensor DNA as a primer is summarized in Table 3 below. This primer is merely characterized in that phosphate is attached at the 5'-end, and the sequence of the primer may be modified as needed, and is not limited to the present example.

TABLE 3

| SEQ ID NO. | Target primer | Primer sequence (5'-3') |
| --- | --- | --- |
| 16 | Hs_RNaseP FW(Forward primer) | [phosphate]CGGCCATCAGAAGGAGATGAAGA |
| 17 | Hs-RNaseP RV(Reverse primer) | [phosphate]AAGGGAGTGCTGACAGAGACTG |
| 18 | Hs_U6 FW | [phosphate]TGCTCGCTTCGGCAGCACATA |
| 19 | Hs-U6 RV | [phosphate]ATATGGAACGCTTCACGAATTTGC |
| 20 | COVID-19 ORF7 FW | [phosphate]TCTTCTGGAACATACGAGGGCA |
| 21 | COVID-19 ORF7 RV | [phosphate]TACGCCGTCAGGACAAGCAA |

TABLE 3-continued

| SEQ ID NO. | Target primer | Primer sequence (5'-3') |
|---|---|---|
| 22 | COVID-19 N gene FW | [phosphate]AAGCTTTCGGCAGACGTGGT |
| 23 | COVID-19 N gene RV | [phosphate]TGCGCGACATTCCGAAGAAC |
| 24 | COVID-19 RdRp gene FW | [phosphate]AGCTCATGGGACACTTCGCA |
| 25 | COVID-19 RdRp gene RV | [phosphate]ATTTGTTCGCGTGGTTTGCC |

Experimental Example 1. Confirming Accuracy of the RNA Detection Technology of the Present Invention in Human Blood RNA was extracted from human blood not infected with COVID-19 using the FavorPrep™ Blood/Cultured Cell Total RNA Mini Kit. It was confirmed whether the target RNA is accurately detected using the method of Example 1.

1 μg of the total RNA extracted as above and 1 fmol of each of the 3 types of sensor DNAs for Hs-RNaseP, Hs-U6, and COVID-19 ORF7 were mixed, and then 2 μl of reaction buffer (200 mM Tris-HCl, 100 mM $(NH_4)_2SO_4$, 100 mM KCl, 20 mM $MgSO_4$, 1% Triton X-100, (pH 8.8 at 25° C.)), 1 μl of 10 mM dNTP and 2 unit XenoT-POL were added and mixed. The mixture was heated at 95° C. for 30 seconds, and then incubated at 63° C. for 10 minutes to generate polymerized strands.

Figure 2:
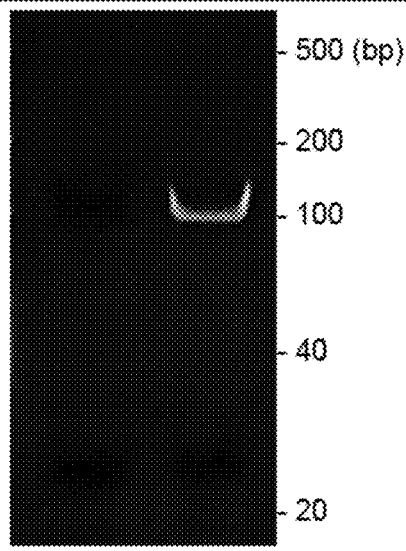
FIG. 2 shows a result confirming the presence of amplicons generated during the process of detecting RNA of the present invention (blood samples from human not infected with COVID-19).

Then, the mixture was cleaned up using the MEGAquick-Spin™ Plus Total Fragment DNA Purification Kit, and eluted with 60 μl of distilled water. In order to observe the amplification of the three polymerized DNA strands in one tube, multiplex PCR was performed. Specifically, primers having the 5'-end capable of amplifying each gene phosphated were used. PCR was performed under the conditions of 1 cycle at 98° C. for 2 minutes, and 35 cycles at 98° C. for 10 seconds and at 62° C. for 10 seconds. After electrophoresis of the PCR product on 10% polyacrylamide gel (19:1), the presence of amplicon, which is the PCR product, was confirmed using Gel Doc (FIG. 2).

Figure 3:
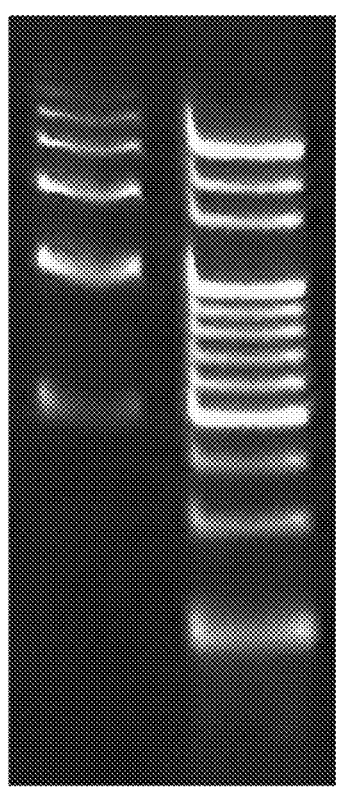
FIG. 3 shows a result confirming that the amplicons generated during the process of detecting RNA of the present invention are ligated (blood samples from human not infected with COVID-19).

After that, the PCR product was cleaned up using the MEGAquick-Spin™ Plus Total Fragment DNA Purification Kit. Then, the cleaned up amplicons were ligated using DNA ligase. 30 μl of 500 ng amplicon, 35 μl of ligation reaction buffer (66 mM Tris-HCl, pH 7.6, 10 mM $MgCl_2$, 1 mM ATP, 1 mM DTT, 7.5% Polyethylene glycol (PEG 6000)), and 1 μl of DNA ligase 100 unit were mixed, and reacted at 25° C. for 20 minutes. After electrophoresis of the ligated product on 10% polyacrylamide gel (29:1), the ligated amplicon was confirmed using Gel Doc (FIG. 3).

The amplicon strands ligated as described above were cleaned up and eluted with 60 μl of distilled water.

40 μl of eluted amplicon DNA strand, 1 μl of 1 mM dATP, 1 μl of taq DNA polymerase (5 unit), 5 μl of reaction buffer (200 mM Tris-HCl/pH 8.8, 500 mM KCl, 25 mM $MgCl_2$, 100 mM β-mercaptoethanol) and distilled water were mixed to make a mixture in 50 μl, and then incubated at 72° C. for 20 minutes and dATP was tailed at the 3' end. Then, adaptor ligation (SQK-LSK109) for nanopore sequencing, clean-up using AMPure XP beads, priming the flow cell, and loading the flow cell processes were performed according to the nanopore sequencing protocol. In the nanopore sequencing file obtained thereafter, the detection result was confirmed by counting the nucleotide sequence of 10 base, which is the complementary sequence of the target RNA barcode in the amplicon region generated based on each target RNA for Hs-RNaseP, Hs-U6, and COVID-19 ORF7.

Figure 4:
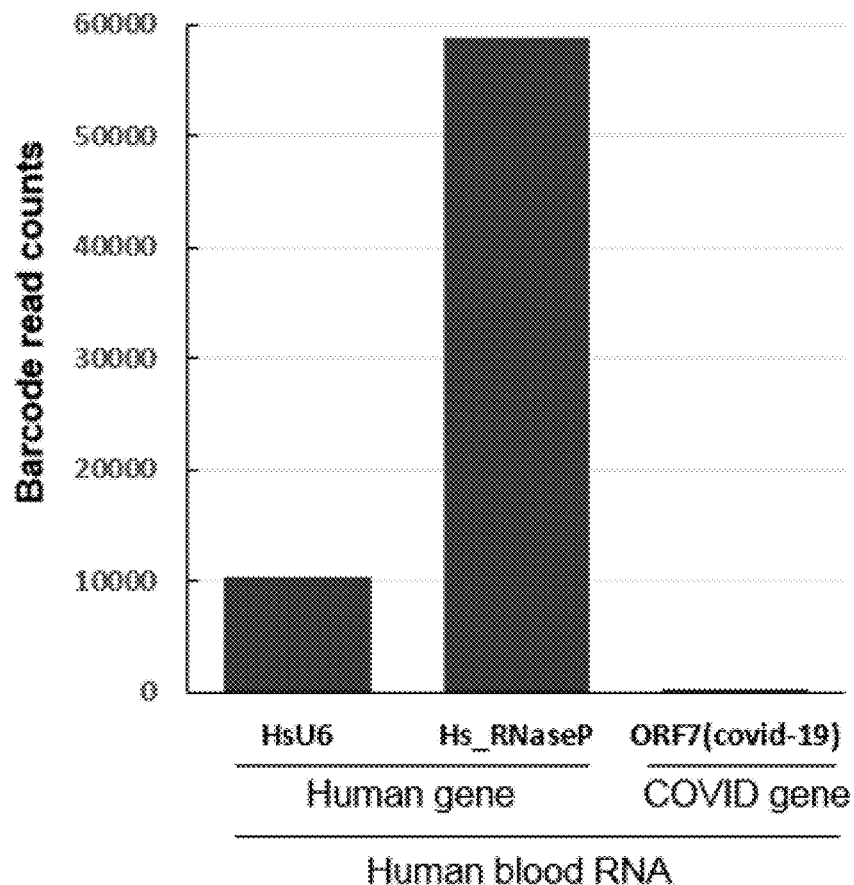
FIG. 4 shows a result confirming the accuracy and sensitivity of the technology of detecting RNA of the present invention in blood samples from human not infected with COVID-19 through quantitative measurement.

As a result, as shown in FIG. 4, the numbers of Hs_U6 and Hs_RNaseP counted were 10,292 and 58,811, and ORF7 of COVID-19, which is used as a negative control (NTC), was not detected.

The above results show that although the concentration of the sensor is remarkably low (1 fmol), the type of RNA can be classified and detected. Accordingly, it was confirmed that the detection limit of the RNA detection technology using the sensor DNA of the present invention is very low and has high sensitivity.

Experimental Example 2. Confirming Accuracy of the RNA Detection Technology of the Present Invention in Virus-Infected Human Blood RNA (NCCP no. 43326) extracted from a human cell line infected with COVID-19 was distributed from the National Pathogen Bank to perform this experiment. It was confirmed whether the target RNA is accurately detected using the method of Example 1.

500 ng of the total RNA and 500 amol of each of the four types of sensors for Hs-RNaseP, COVID-19 ORF7, COVID-19 N gene and COVID-19 RdRp gene were mixed, and then 2 μl of reaction buffer (200 mM Tris-HCl, 100 mM $(NH_4)_2SO_4$, 100 mM KCl, 20 mM $MgSO_4$, 1% Triton X-100, (pH 8.8 at 25° C.)), 1 μl of 10 mM dNTP and 2 unit XenoT-POL were added and mixed. The mixture was heated at 95° C. for 30 seconds, and then incubated at 63° C. for 10 minutes to generate polymerized strands.

Figure 5:
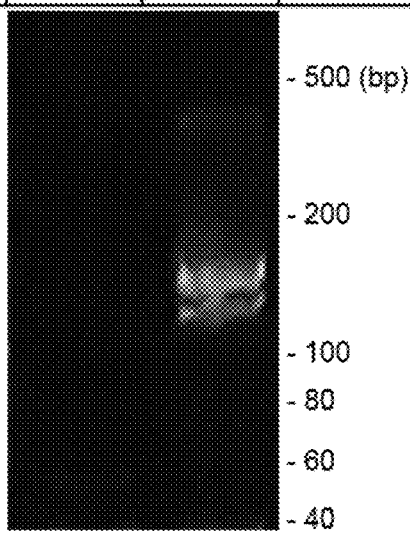
FIG. 5 shows a result confirming the presence of amplicons generated during the process of detecting RNA of the present invention (blood samples from human infected with COVID-19).

Then, the mixture was cleaned up using the MEGAquick-Spin™ Plus Total Fragment DNA Purification Kit, and eluted with 60 μl of distilled water. In order to observe the amplification of the four polymerized DNA strands in one tube, multiplex PCR was carried out. Specifically, primers having the 5'-end capable of amplifying each gene phosphated were used. PCR was performed under the conditions of 1 cycle at 98° C. for 2 minutes, and 35 cycles at 98° C. for 10 seconds and at 62° C. for 10 seconds. After electrophoresis of the PCR product on 10% polyacrylamide gel (19:1), the presence of amplicon, which is the PCR product, was confirmed using Gel Doc (FIG. 5).

Figure 6:
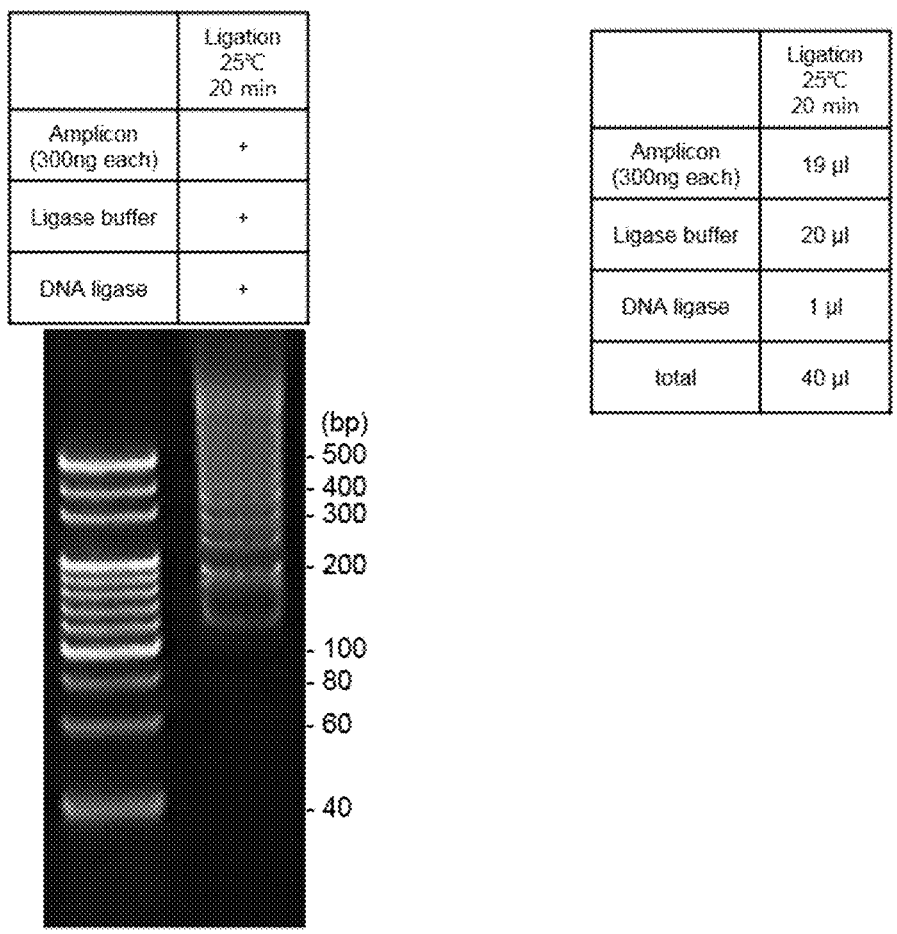
FIG. 6 shows a result confirming that the amplicons generated during the process of detecting RNA of the present invention are ligated (blood samples from human infected with COVID19).

After that, the PCR product was cleaned up using the MEGAquick-Spin™ Plus Total Fragment DNA Purification Kit. Then, the cleaned up amplicons were ligated using DNA ligase. 19 μl of 300 ng amplicon, 35 μl of ligation reaction buffer (66 mM Tris-HCl, pH 7.6, 10 mM $MgCl_2$, 1 mM ATP, 1 mM DTT, 7.5% Polyethylene glycol (PEG 6000)), and 1 μl of DNA ligase 100 unit were mixed, and reacted at 25° C. for 20 minutes. After electrophoresis of the ligated product on 10% polyacrylamide gel (29:1), the ligated amplicon was confirmed using Gel Doc (FIG. 6).

The amplicon strands ligated as described above were cleaned up and eluted with 60 μl of distilled water.

40 μl of eluted amplicon DNA strand, 1 μl of 1 mM dATP, 1 μl of taq DNA polymerase (5 unit), 5 μl of reaction buffer (200 mM Tris-HCl/pH 8.8, 500 mM KCl, 25 mM $MgCl_2$, 100 mM β-mercaptoethanol) and distilled water were mixed to make a mixture in 50 μl, and then incubated at 72° C. for 20 minutes and dATP was tailed at the 3' end. The dATP tailed DNA product was cleaned up using the MEGAquick-Spin™ Plus Total Fragment DNA Purification Kit.

Then, adaptor ligation (SQK-LSK109) for nanopore sequencing, clean-up using AMPure XP beads, priming the flow cell, and loading the flow cell processes were performed according to the nanopore sequencing protocol. In the nanopore sequencing file obtained thereafter, the detection result was confirmed by counting the nucleotide sequence of 10 base, which is the complementary sequence of the target RNA barcode in the amplicon region generated based on each target RNA for Hs-RNaseP, COVID-19 ORF7, COVID-19 N gene and COVID-19 RdRp.

Figure 7:
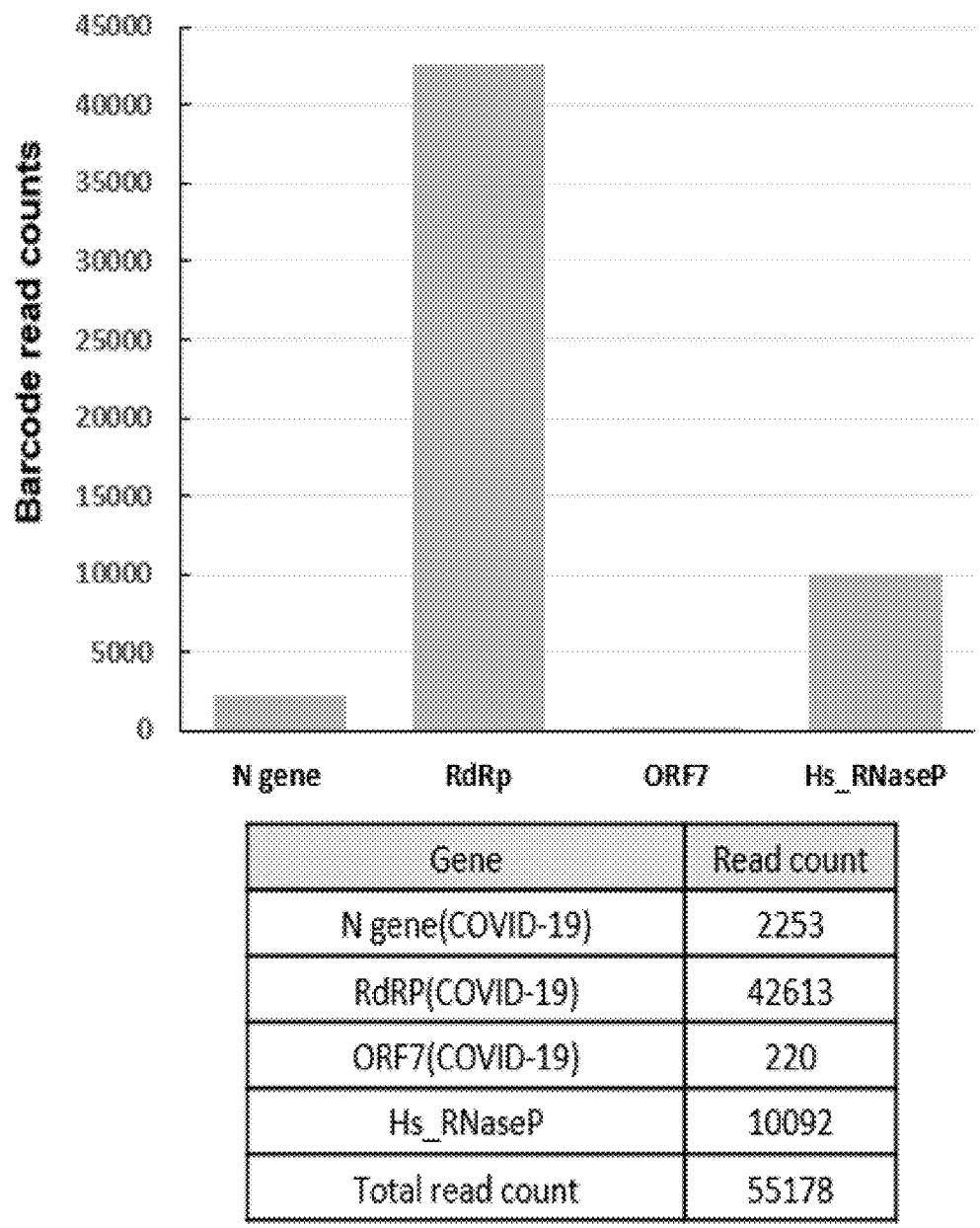
FIG. 7 shows a result confirming the accuracy and sensitivity of the technology of detecting RNA of the present invention in blood samples from human infected with COVID-19 through quantitative measurement.

As a result, as shown in FIG. 7, 2,253 N genes (COVID-19), 42,613 RdRps (COVID-19), 220 ORF7s (COVID-19), and 10,092 Hs_RNasePs were counted.

The above results show that although the concentration of the sensor is remarkably low (500 amol), not only can the type of RNA be classified and detected, but also viral infection may be diagnosed. From the above, it was confirmed that the RNA detection technology using the sensor DNA of the present invention may diagnose whether a patient is infected with RNA virus with a very low detection limitation and high sensitivity. In particular, the RNA detection technology of the present invention confirmed that the amount quantitatively detected varies according to the viral gene region, beyond simply identifying the presence or absence of RNA, and thus may be applied to identifying the expression level of the gene site to diagnose the infection level.

The above results show that the technology of the present invention may quickly diagnose normal, disease onset period, latent period, outbreak period, etc. at molecular levels by measuring the presence of RNA, which is an indicator of infectious diseases, cancer caused by virus, bacteria, etc., at a quantitative level rather than simply detecting RNA.

In particular, the features of the method of detecting RNA and the sensor DNA used for detection in the present invention show a very low detection limitation at levels of femtomole (fmol) and attomole (amol), and thus the sensitivity and accuracy are remarkably superior to the conventional techniques for detecting RNA.

Accordingly, the present invention overcomes the detection limitations of the existing technologies such as diagnosis of a disease in individuals such as human, progress of a disease, diagnosis of viral infection in latent period, etc. by enabling molecular diagnosis at a minute level, and thus may be usefully used even for diagnosis at a very early stage or latent period of a disease.

The above-described description of the present invention is provided for illustrative purposes, and those skilled in the art to which the present invention pertains will understand that the present invention can be easily modified into other specific forms without changing the technical spirit or essential features of the present invention.

Therefore, it should be understood that the above-described embodiments are only exemplary in all aspects and are not restrictive. For example, each constituent element which is described as a singular form may be implemented in a distributed form, and similarly, constituent elements which are described as being distributed may be implemented in a combined form.

The scope of the present invention is represented by the claims to be described below, and it should be interpreted that the meaning and scope of the claims and all the changes or modified forms derived from the equivalent concepts thereof fall within the scope of the present invention.

What is claimed is:

1. A method of detecting RNA, comprising:
   a) hybridizing a sensor DNA comprising a complementary sequence of a target RNA to be detected with the target RNA such that the sensor DNA complementarily binds to the target RNA;
   b) one cycle of polymerization with a polymerase using the target RNA as a template and the sensor DNA as a primer;
   c) generating a plurality of amplicons by amplifying using a primer complementary to the strand polymerized in step b); and
   d) analyzing the sequence of the plurality of amplicons,
   d') ligating the plurality of amplicons; and
   e) analyzing a sequence of the ligated amplicons after step d'), and
   wherein the respective amplicon that is amplified comprises a sequence complementary to a barcode region of the target RNA,
   wherein the step b) is performed only once in the method of detecting RNA,
   wherein the sensor DNA is in an amount of 500 amol to 1 fmol, and
   wherein the primer in step c) has a phosphate group covalently attached to the 5' end.

2. The method of claim 1, wherein step d') further comprising, after ligation of the plurality of amplicons, binding an adaptor for sequencing to both ends of the ligated amplicons.

3. The method of claim 1, wherein step e) comprises a nanopore sequencing.

4. The method of claim 1, further comprising, before step a), designating a unique barcode region in the target RNA.

5. The method of claim 1, further comprising quantitatively detecting a number of target RNAs by measuring a number of amplicons.

6. The method of claim 5, wherein the number of amplicons is confirmed by measuring the number of sequences complementary to the barcode region comprised in the amplicons.

* * * * *